(12) United States Patent
Berg et al.

(10) Patent No.: US 7,696,381 B1
(45) Date of Patent: Apr. 13, 2010

(54) ALTERNATIVE DIMERISATION REAGENTS FOR SYNTHESIS OF IODIXANOL

(75) Inventors: Arne Berg, Blommenholm (NO); Harald Dugstad, Oslo (NO); Michel Gacek, Hovik (NO); Trygve Gulbrandsen, Kolsas (NO); Per Strande, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 12/565,785

(22) Filed: Sep. 24, 2009

Related U.S. Application Data

(60) Provisional application No. 61/227,099, filed on Jul. 21, 2009.

(51) Int. Cl.
*C07C 233/65* (2006.01)
*C07C 233/05* (2006.01)

(52) U.S. Cl. ..................................... 564/153; 424/9.452

(58) Field of Classification Search ................. 564/153; 424/9.452
See application file for complete search history.

(56) References Cited

U.S. PATENT DOCUMENTS

| 6,974,882 B2 | 12/2005 | Homestad |
| 2002/0010368 A1 | 1/2002 | Homestad |

FOREIGN PATENT DOCUMENTS

| EP | 0108638 | 5/1984 |
| KR | 2004-0087044 | 10/2004 |
| KR | 2005-0006367 | 1/2005 |
| KR | 2005-0024944 | 3/2005 |
| WO | WO 00/47549 | 8/2000 |

*Primary Examiner*—Shailendra Kumar

(57) ABSTRACT

This invention relates generally to non-ionic X-ray contrast agents. It further relates to the synthesis of iodixanol. In particular, it relates to alternative dimerisation reagents in the conversion of 5-acetamido-N,N'-bis(2,3-dihydroxypropyl)-2,4,6-triiodoisophthalamide ("Compound A") to iodixanol.

3 Claims, No Drawings

ALTERNATIVE DIMERISATION REAGENTS FOR SYNTHESIS OF IODIXANOL

CROSS REFERENCE TO RELATED APPLICATIONS

The present application claims benefit of priority under 35 U.S.C. §119(e) to U.S. Provisional Application No. 61/227,099 filed Jul. 21, 2009, the entire disclosure of which is hereby incorporated by reference.

TECHNICAL FIELD

This invention relates generally to non-ionic X-ray contrast agents. It further relates to the synthesis of iodixanol. In particular, it relates to alternative dimerisation reagents in the conversion of 5-acetamido-N,N'-bis(2,3-dihydroxypropyl)-2,4,6-triiodoisophthalamide ("Compound A") to iodixanol.

BACKGROUND OF THE INVENTION

Iodixanol (1,3-bis(acetamido)-N,N'-bis[3,5-bis(2,3-dihydroxypropylaminocarbonyl)-2,4,6-triiodophenyl]-2-hydroxypropane) is a non-ionic X-ray contrasting agent produced in large quantities by GE Healthcare in Lindesnes, Norway. The traditional industrial synthesis of iodixanol involves dimerisation of intermediate 5-acetamido-N,N'-bis(2,3-dihydroxypropyl)-2,4,6-triiodoisophthalamide ("Compound A") as the final synthetic step. See Scheme 1 and U.S. Pat. No. 6,974,882.

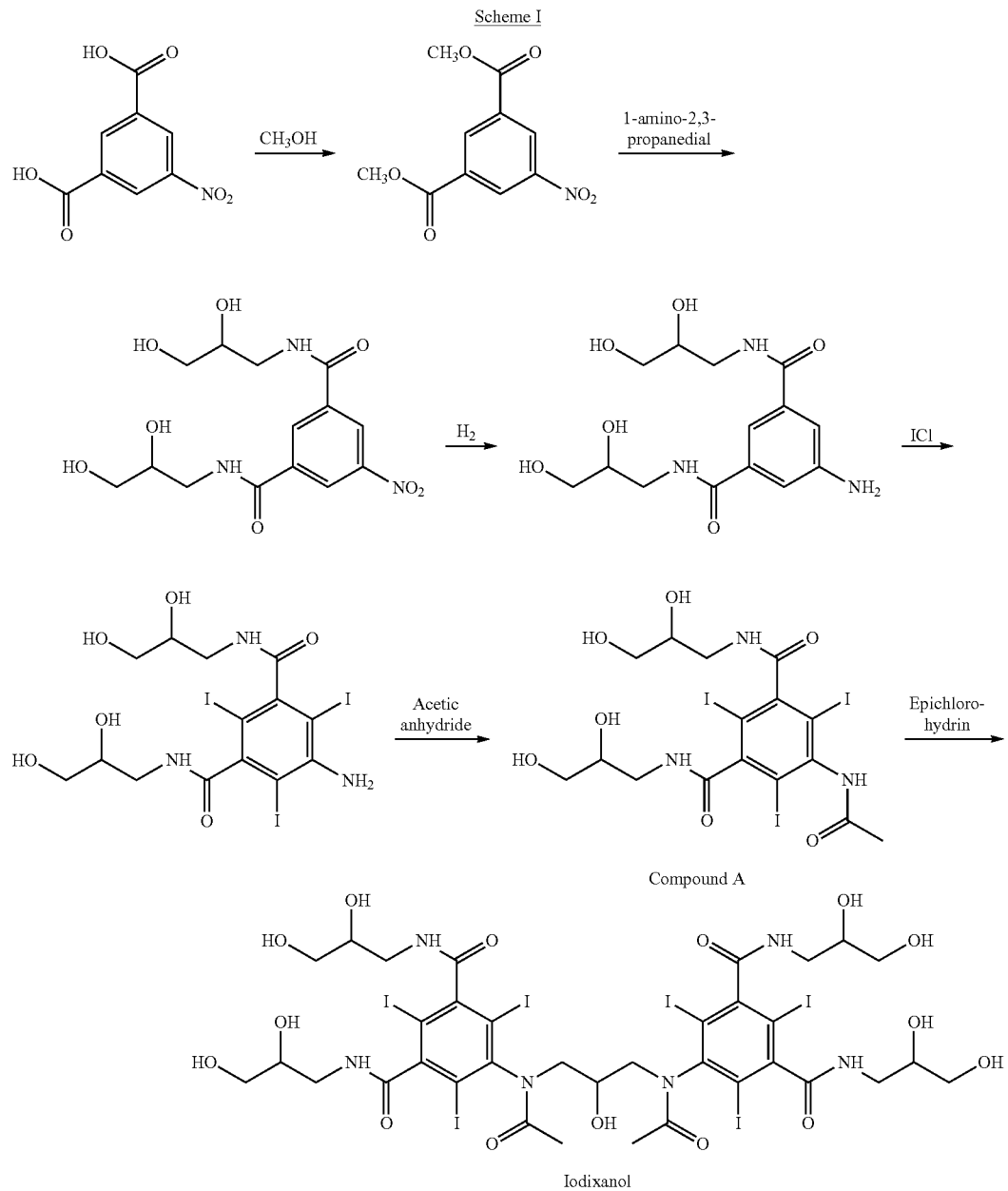

Scheme I

Currently, the only dimerisation agent used in an industrial production of iodixanol is epichlorohydrin, shown below.

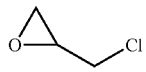

It is thus desirable to develop alternative dimerisation reagents that are suitable for conversion of Compound A to iodixanol with acceptable yield.

SUMMARY OF THE INVENTION

The present invention provides a process for preparing iodixanol by dimerisation of Compound A using 1,3-dichloropropanol, 1,3-dibromopropanol, 1,3-diiodopropanol, THP protected 1,3-dichloropropanol (THP being tetrahydropyrane), THP protected 1,3-dibromopropanol, THP protected 1,3-diiodo propanol, acetoxy protected 1,3-dichloropropanol (acetoxy being $COCH_3$), acetoxy protected 1,3-dibromopropanol, acetoxy protected 1,3-diiodopropanol, MOM protected 1,3-dichloropropanol (MOM being $CH_2OCH_3$), MOM protected 1,3-dibromopropanol, MOM protected 1,3-diiodopropanol, or dichloroacetone as the dimerisation agent. The instant dimerisation reaction is performed under alkaline conditions with pH values between about 10 and about 12.

DETAILED DESCRIPTION OF THE INVENTION

The dimerisation reaction time of the present invention may vary from a few hours to several days. The dimerisation may proceed to full or partial conversion. Typical reaction temperatures may range from about 5° C. to about 50° C., preferably between about 10 and about 25° C. In addition, a lower reaction temperature may be preferred when selectivity (the ratio of iodixanol and impurities such as trimers and O-alkylated compounds) is desired.

The invention is illustrated further by the following examples that are not to be construed as limiting the invention in scope to the specific procedures or products described in them.

EXAMPLES

Example 1

Acetoxy Protected 1,3-dibromopropanol

The sodium salt of Compound A was dissolved in dry DMAc at room temperature before 1,3-dibromo-2-acetoxypropane was added at the same temperature. A slow pH change was observed from 11.9 to 10.4. After 16 hours anhydrous $K_2CO_3$ was added and the reaction was continued for an additional time before being worked up in the usual manner.

The calcium salt of Compound A was prepared in situ and after addition of 1,3-dibromo-2-acetoxypropane the reaction was carried out at 50° C.

Example 2

THP Protected 1,3-dichloropropanol

Compound A (12.5 g, 16.7 mmol) was dissolved in DMAc (38 ml), and NaH (0.5 g, 1.1 eq) was added over a period of 15 min. Following the addition, the mixture was stirred at room temperature for 15 min before THP protected 1,3-dichloropropanol was added and the temperature raised to 80° C. NaI (0.25 g, 0.1 eq) was added after 3 days. About 35% conversion of Compound A was obtained after 6 days.

Example 3

1,3-dichloropropanol

Compound A is dissolved in 2-methoxyethanol (0.8-1.2 mL/g Compound A) in the presence of NaOH. pH is adjusted to about 11.8-12.0 with hydrochloric acid, and 1,3-dichloropropanol (about 0.33 eq) is added. The reaction is conducted at 15° C. for about 40 hours. A conversion of about 55% of the starting material Compound A to iodixanol is observed, with only 1-2% of byproducts formed.

All patents, journal articles, publications and other documents discussed and/or cited above are hereby incorporated by reference.

We claim:

1. A process for preparing iodixanol by dimerisation of 5-acetamido-N,N'-bis(2,3-dihydroxypropyl)-2,4,6-triiodo-isophthalamide (Compound A) using THP protected 1,3-dichloropropanol as the dimerisation agent under alkaline conditions with pH values between about 10 and about 12.

2. A process for preparing iodixanol by dimerisation of 5-acetamido-N,N'-bis(2,3-dihydroxypropyl)-2,4,6-triiodo-isophthalamide (Compound A) using THP protected 1,3-dibromopropanol, or acetoxy protected 1,3-dibromopropanol, as the dimerisation agent under alkaline conditions with pH values between about 10 and about 12.

3. A process for preparing iodixanol by dimerisation of 5-acetamido-N,N'-bis(2,3-dihydroxypropyl)-2,4,6-triiodo-isophthalamide (Compound A) using 1,3-diiodopropanol, THP protected 1,3-diiodopropanol, or acetoxy protected 1,3-diiodopropanol, as the dimerisation agent under alkaline conditions with pH values between about 10 and about 12.

* * * * *